United States Patent [19]

McLennan Anderson

[11] Patent Number: 4,909,248

[45] Date of Patent: Mar. 20, 1990

[54] TRACHEAL TUBE FITTINGS AND ASSEMBLIES

[75] Inventor: Gregor J. McLennan Anderson, Folkestone, England

[73] Assignee: Smiths Industries Public Limited Company, London, England

[21] Appl. No.: 294,706

[22] Filed: Jan. 9, 1989

[30] Foreign Application Priority Data

Jan. 9, 1988 [GB] United Kingdom ............... 8800446
Jul. 23, 1988 [GB] United Kingdom ............... 8817593

[51] Int. Cl.$^4$ ............................................ A61M 16/00
[52] U.S. Cl. ........................... 128/207.14; 128/200.26; 128/912; 128/207.15
[58] Field of Search ............ 128/207.14, 207.15, 128/207.16, 200.26, 912, 202.18; 623/9; 285/924, 153, 154, 13, 14, 7; 604/283, 129, 10, 327, 269; 239/DIG. 21, DIG. 22

[56] References Cited

U.S. PATENT DOCUMENTS

| | | | |
|---|---|---|---|
| 1,065,920 | 7/1913 | Crowe | 128/207.14 |
| 2,039,142 | 4/1936 | Brehm | 128/207.16 |
| 2,269,823 | 1/1942 | Kreiselman | 128/207.15 |
| 2,393,326 | 1/1946 | Lane | 128/202.18 |
| 2,491,647 | 12/1949 | Colavita | 604/327 |
| 2,862,498 | 12/1958 | Weekes | 128/207.14 |
| 3,066,674 | 12/1962 | Capra | 623/9 |
| 3,807,401 | 4/1974 | Riggle et al. | 604/269 |
| 3,952,335 | 4/1976 | Sorce et al. | 623/9 |
| 4,243,178 | 1/1981 | Self | 239/DIG. 22 |
| 4,261,516 | 4/1981 | Tillman | 239/DIG. 21 |
| 4,456,016 | 1/1984 | Nowacki et al. | 128/207.16 |
| 4,490,138 | 12/1984 | Lipsky et al. | 285/7 |
| 4,582,058 | 4/1986 | Depel et al. | 128/207.16 |
| 4,725,268 | 2/1988 | Ostensen et al. | 604/129 |
| 4,759,356 | 7/1988 | Muir | 623/9 |
| 4,802,474 | 2/1989 | Beevers | 128/207.14 |

FOREIGN PATENT DOCUMENTS

| | | | |
|---|---|---|---|
| 48686 | 5/1974 | Australia | 239/DIG. 21 |
| 0107861 | 3/1964 | Netherlands | 623/9 |
| 1174397 | 12/1969 | United Kingdom | |

*Primary Examiner*—Edgar S. Burr
*Assistant Examiner*—Aaron J. Lewis
*Attorney, Agent, or Firm*—Pollock, Vande Sande & Priddy

[57] ABSTRACT

An anti-occlusion fitting for a paediatric tracheostomy tube has concentric inner and outer tubular members. The distal end of the inner member is push fitted onto the tube; the proximal end extends beyond the outer member and has channels across its end which form openings into an annular air passage between the inner and outer members. The outer member has opening through its wall, in two annular grooves around its outer surface, so that air can flow into the tube via the openings, the air passage and the channels if the proximal end of the fitting is occluded. Connection can be made to the tube by female connectors of different size pushed onto the inner or outer tubular members.

10 Claims, 4 Drawing Sheets

TRACHEAL TUBE FITTINGS AND ASSEMBLIES

BACKGROUND OF THE INVENTION

This invention relates to fittings for tracheal tubes and to tracheal tube assemblies including such fittings.

The invention is more particularly concerned with tracheostomy tubes and fittings for paediatric use which are arranged to reduce the risk of occlusion.

Where tracheostomy tubes are used with young children there is a substantial risk of the tube becoming blocked at the patient's neck by folds of skin contacting the open end of the tube or by the child touching the end of the tube.

BRIEF SUMMARY OF THE INVENTION

It is an object of the present invention to provide a tracheal tube fitting and assembly that can be used to reduce the risk of occlusion of the tube.

According to one aspect of the present invention there is provided a fitting for the proximal end of a tracheal tube the distal end of which is adapted for location in the trachea of a patient, the fitting comprising an inner member having a distal end adapted to be fitted in the proximal end of the tube and a proximal end that is open, an outer member surrounding the inner member and having an air passage therebetween, the outer member having an open proximal end, the inner member having at least one opening therethrough into the air passage, and the outer member having at least one opening therethrough into the air passage, to enable gas to flow between the tube and atmosphere via the openings and the air passage when the proximal end of the inner and outer members are obstructed.

The inner and outer members are preferably of circular section, the inner and outer members being adapted to receive connectors thereon as a push fit, such as to enable connection with the tracheal tube by different diameter connectors. The proximal end of the inner member may project beyond the proximal end of the outer member. The opening through the inner member may be provided by a channel across the proximal end of the inner member. A part at least of the channel preferably extends with the proximal end of the outer member. The opening through the outer member may communicate with a groove that extends around the major part of the outer surface of the outer member. The outer member may have two grooves extending around the major part of the outer surface of the outer member and separated from one another by an annular wall, the outer member having an opening through the outer member within each groove.

The outer member may be removable from the inner member. The outer member and the inner member may be retained with one another by means of a screw threaded engagement. The outer member may have a screw thread on an inner surface and the inner member having a flange with a surface formation that engages the screw thread.

According to another aspect of the present invention there is provided a tracheostomy tube assembly including a tracheostomy tube the distal end of which is adapted for location in the trachea of a patient through a surgically made opening in the trachea, and a fitting according to the above one aspect of the invention fitted on the proximal end of the tube.

A tracheostomy tube assembly inc;luding a fitting according to the present invention will now be described, by way of example with reference to the accompanying drawings.

DETAILED DESCRIPTION

Figure 1:
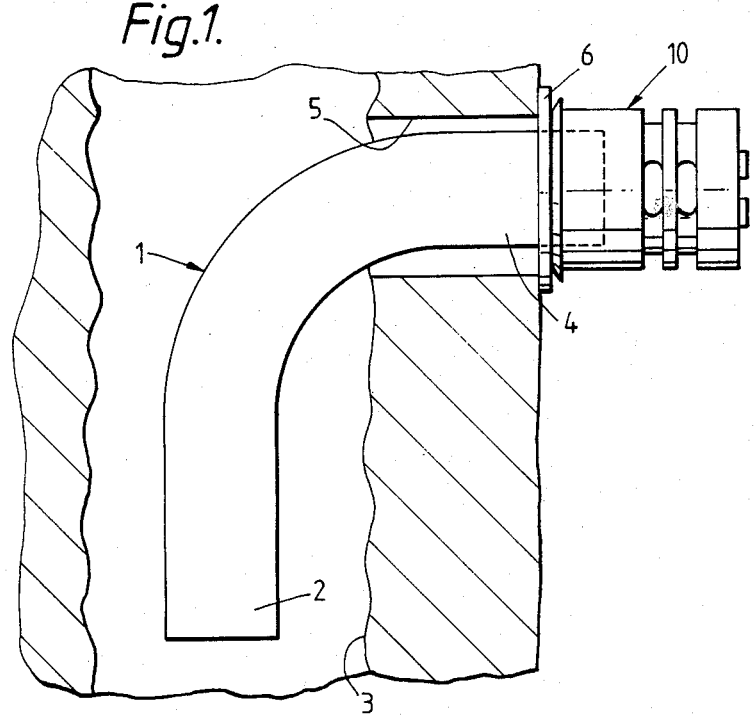
FIG. 1 is a side elevation view of the assembly in use.

With reference to FIG. 1, the tracheostomy tube 1 is of uncuffed form for paediatric use having a square, open patient or distal end 2 that is located, in use, in the trachea 3 of the patient. The machine or proximal end 4 of the tube extends through a surgically made opening 5 between the trachea and the surface of the patient's neck. A flange 6 is mounted at the proximal end 4 of the tube which lies against the surface of the patient's neck and which is secured to the neck by means of a tape (not shown), to stabilise the tube. The proximal end 4 of the tube is terminated by a fitting 10 which serves to prevent accidental occlusion of the tube.

Figure 2:
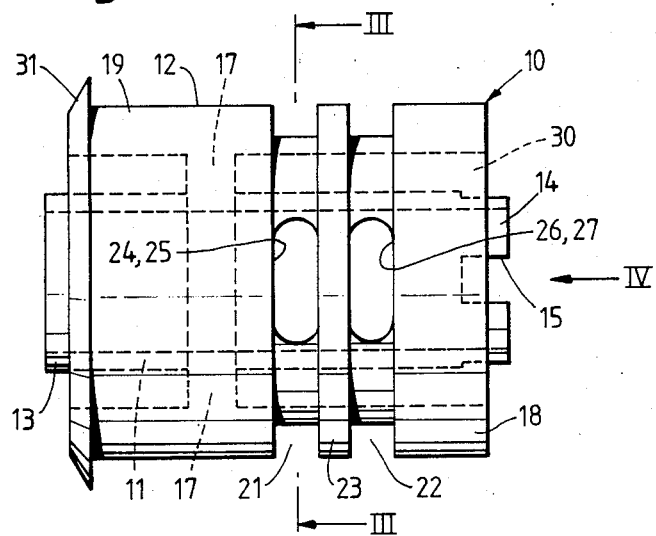
FIG. 2 is a side elevation view of the present invention fitting to an enlarged scale.
Figure 3:
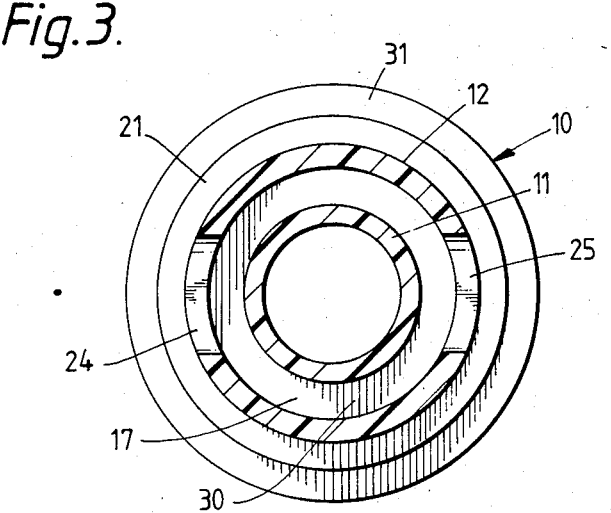
FIG. 3 is a transverse section through the fitting along the line III—III.
Figure 4:
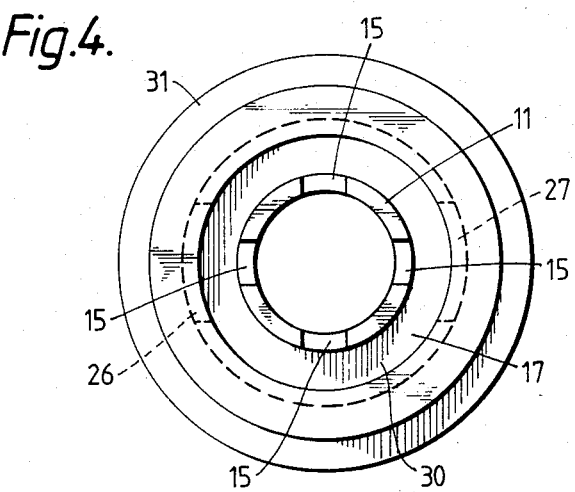
FIG. 4 is an end view of the fitting along the arrow IV.

With reference also to FIGS. 2 to 4, the fitting 10 is a generally cylindrical moulding of a rigid plastics material such as nylon. The fitting comprises coaxial inner and outer tubular members 11 and 12. The inner member 11 is open at both ends and is of circular section with an external diameter of 8.5 mm, an internal diameter of 5 mm and an overall length of 20 mm. The distal end 13 of the inner member projects from the distal end of the outer member 12 by about 1 mm. The proximal end 14 of the inner member projects from the proximal end of the outer member by about 1 mm and has four radial channels 15 equally disposed around it. The channels 15 have a depth of about 2 mm and give the proximal end of the inner member a castellated appearance.

The inner member 11 is supported on the outer member 12 by a radially extending annular flange 17 located about 7 mm from the distal end 13 of the inner member 11. The outer member 12 is shorter than the inner member, being 18 mm long with a circular section, an outer diameter of 15 mm and an inner diameter of 11 mm. The proximal end 18 of the outer member 12 is open, whereas it is closed towards its distal end 19 by the flange 17. Around the outer surface of the outer member 12 are formed two annular grooves 21 and 22 of width about 2 mm and depth about 1.5 mm, the grooves being located about 4 mm from the proximal end of the outer member and separated from one another by an annular wall 23 of width about 1.5 mm. In the floor of both grooves 21 and 22 are formed two slots 24 and 25, and 26 and 27 respectively which provide elongate openings through the wall of the outer member 12 into an annular recess 30 between the inner and outer members. At the distal end of the outer member 12 there is an outwardly projecting lip 31 of height about 1.5 mm.

In use, the distal end 13 of the inner member 11 is pushed into the proximal end 4 of the tube 1, its diameter being such as to form a fluid-tight push fit on the tube. The extent of insertion into the tube 1 is limited by engagement of the tube 1 with the flange 17 in the fitting 10, and by engagement of the distal end of the outer tubular member 12 with the flange 6 on the tube. The tracheostomy tube assembly formed by the inclusion of the fitting 10 is far less prone to occlusion than a tracheostomy tube without the fitting.

In normal use, air flows into and out of the tube 1 via the bore through the inner member 11 and via its open proximal end 14. If, however, the proximal end 14 of the inner member is blocked, such as by light pressure from a fold of skin, air will still be able to enter and leave the inner member through the channels 15. If greater pressure is exerted so that the proximal end 18 of the outer member 12 is also blocked, air will still be able to flow into the inner member 11 through the slots 24 to 27 in the outer member, via the annular air passage 30 between the two members and via the channels 15. Even if some part of the body overlies the outer member in the region of the slots 24 to 27, air will still be able to enter the slots via the external grooves 21 and 22, since the grooves and the intervening wall 23 prevent direct contact with the slots 24 to 27. This construction reduces the risk of occlusion if the patient should touch or hold the end of the assembly.

Figure 2A:
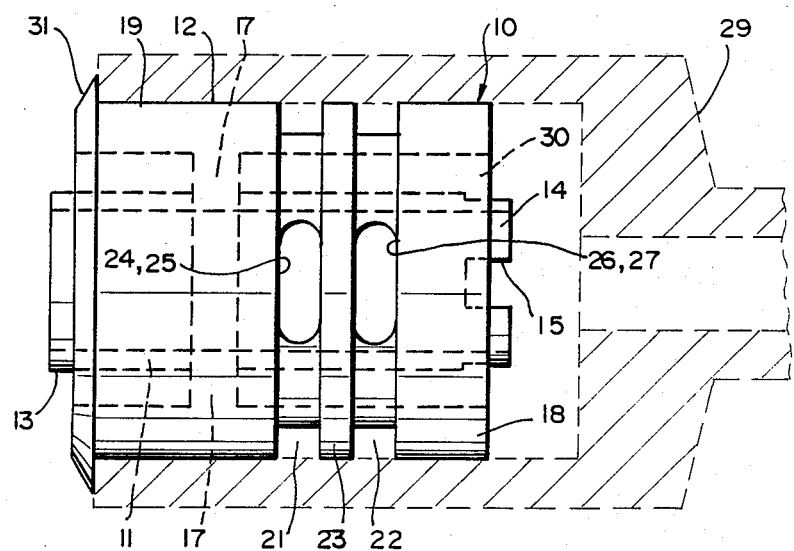
FIG. 2a is a side elevation view of the fitting as shown in FIG. 2a with an outer connector.
Figure 2B:
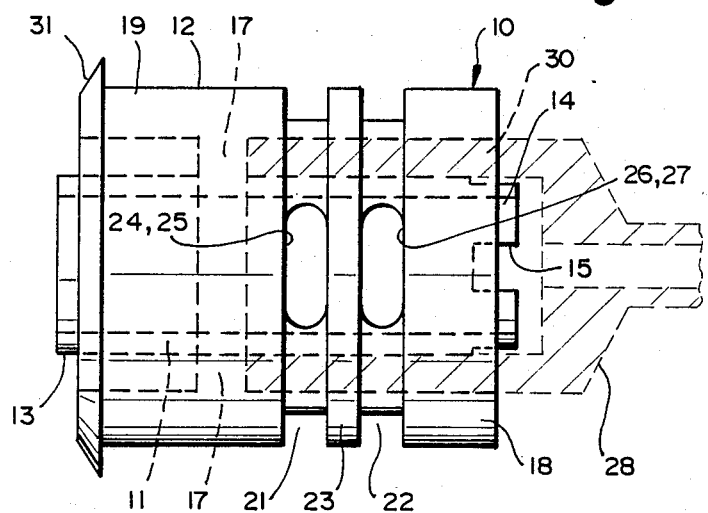
FIG. 2b is a side elevation view of the fitting as shown in FIG. 2b with an inner connector.

The fitting 10, in addition to preventing occlusion also serves the purpose of providing a tubing adaptor for use in making external connection with the tracheostomy tube. Connection can be made by standard female taper connectors of either 8.5 mm or 15 mm diameter. The smaller connector 28 would be pushed over the proximal end of the inner member 11 as shown in FIG. 2b. The larger diameter connector 29, as shown in FIG. 2a would be pushed onto the outer member 12 far enough to cover both grooves 21 and 22, the lip 31 providing an abutment for the connector such that gas flows to the atmosphere through the openings in the outer connector would be prevented. The fitting 10 thereby enables connection to connectors of two different diameters. This has considerable advantages in emergencies where the small diameter paediatric connectors may not be readily available.

Figure 5:
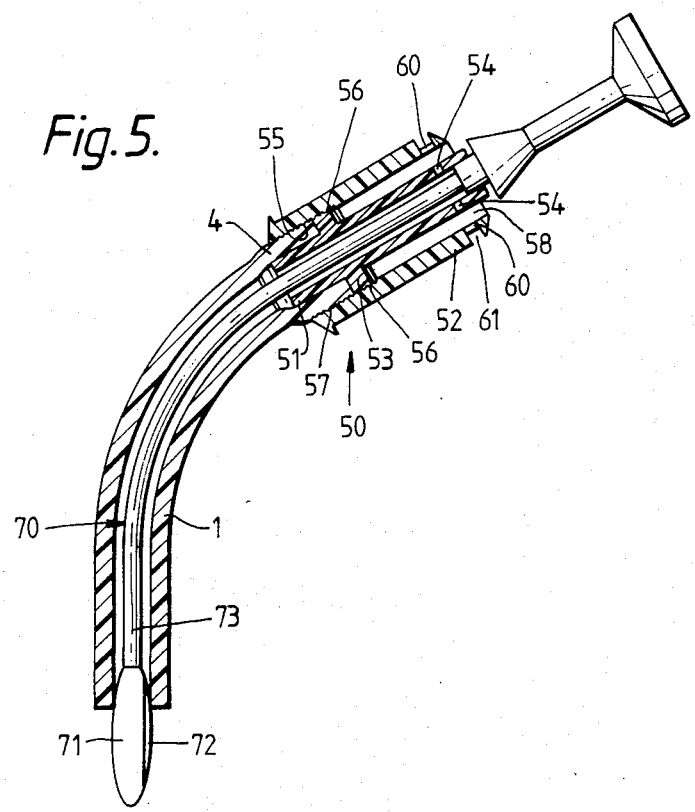
FIG. 5 is a sectional side elevation view of an alternative assembly.
Figure 6:
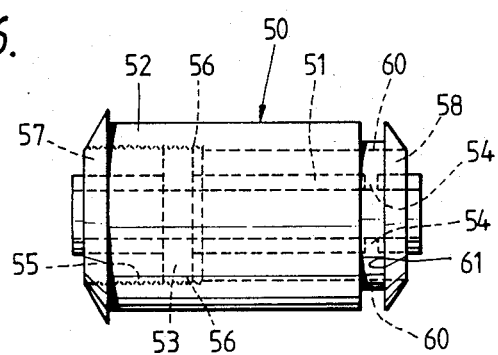
FIG. 6 is a side elevation view of the fitting of FIG. 5.

The fitting could be made in two parts, as shown in FIGS. 5 and 6. In this arrangement, the fitting 50 comprises an inner part 51 and an outer sleeve 52 that is screwed onto the inner part. The inner part 51 is of cylindrical, tubular shape with a radial flange 53 about one third of the way along its length. The end forwardly of the flange 53 is a push fit in the machine end 4 of the tube 1. The rear end of the inner part 51 has two apertures 54 extending through its wall which are located diametrically opposite one another a short distance from the rear end.

The outer sleeve 52 has a screw threaded region 55 at the forward end of its inner surface which engages with two lugs 56 projecting radially outwardly from the flange 53 on the inner part 51. The outer sleeve 52 extends coaxially of the inner part 51 forming an annular recess 57 at the forward end of the fitting 50, in which the machine end 4 of the tube 1 is received. The outer sleeve 52 terminates a short distance forwardly of the rear end of the inner part 51 and also forms an annular recess 58 at the rear end of the fitting. Two slots 60 extend through the wall of the sleeve 52, approximately level with the apertures 54 in the inner part. The slots 60 lie in an annular groove 61 around the outer surface of the sleeve which functions in the same way as the grooves 21 and 22 in the arrangement shown in FIGS. 1 to 4.

By making the outer sleeve removable from the inner sleeve, this facilitates cleaning of the fitting 50. Also, the outer sleeve can be removed completely if desired, where the fitting 50 is connected to a 8.5 mm female connector.

The location of the apertures 54 is chosen so that they are not blocked when an abturator 70 is inserted in the tube 1. The obturator 70 has a pointed tip 71 that projects from the forward end of the tube 1 to guide the tube during insertion through a surgically made opening in the trachea. The tip 71 has a slot 72, or other air passage, that permits flow of air into the tube 1. The tip 71 is located at the forward end of a flexible stem 73 which allows airflow along the tube, either by being of smaller diameter, as shown, or by the provision of an air passage along the stem itself. Air flowing along the tube can flow out via the apertures 54 and the slots 60 or the rear end of the sleeve 52. This ensures that the patient is free to breathe even while the tube is being introduced. It will be appreciated that an air passage at the rear end of the tube and obturator assembly could be provided in other ways, such as, for example, by shaping the rear end of the obturator so that it does not occlude the rear end of the fitting when in use.

What is claimed is:

1. A tracheal tube assembly comprising: a tracheal tube, the tracheal tube having a proximal end and a distal end, said distal end being adapted for location in the trachea of a patient; and a fitting secured in the proximal end of the tube, wherein said fitting comprises an inner member, said inner member having a distal end and a proximal end, said distal end being fitted in said proximal end of the tube and said proximal end being open; and an outer member, said outer member substantially surrounding the inner member and having an air passage therebetween said outer member being of circular section shaped to receive a first connector thereon as a push fit, said outer member having a proximal end, said proximal end being open, and wherein said inner member has at least one opening therethrough into said air passage, and said outer member has at least one opening therethrough into said air passage, such that the gas can flow between the tube and atmosphere via the openings and the air passage when said proximal end of the inner and outer members are obstructed and such that gas flow to the atmosphere via the openings in the outer member is provided when said first connector is fitted on said outer member.

2. A fitting according to claim 1, where said inner member is of circular section, and wherein the inner member is shaped to receive a second connector thereon as a push fit, said second connector having a smaller diameter than said first connector.

3. A fitting according to claim 1, wherein the proximal end of the inner member projects beyond the proximal end of the outer member.

4. A fitting according to claim 1, wherein the opening through the inner member is provided by a channel across the proximal end of the inner member.

5. A fitting according to claim 4, wherein a part at least of said channel extends within the proximal end of the outer member.

6. A fitting according to claim 1, wherein said outer member has an outer surface and a groove that extends around the major part of the outer surface, and wherein the opening through the outer member communicates with said groove.

7. A fitting according to claim 6, wherein the outer member has two grooves extending around the major part of the outer surface of the outer member, wherein the two said grooves are separated from one another by an annular wall, and wherein the outer member has an opening through the outer member within each groove.

8. A fitting according to claim 1, wherein the said outer member is removable from the inner member.

9. A fitting according to claim 8, wherein the outer member and the inner member are retained with one another by means of a screw threaded engagement.

10. A tracheal tube assembly comprising: a tracheal tube, the tracheal tube having a proximal end and a distal end, said distal end being adapted for location in the trachea of a patient; and a fitting secured in the proximal end of the tube, wherein said fitting comprises an inner member, said inner member having a distal end and a proximal end, said distal end being fluid-tight push-fitted into said proximal end of the tube and said proximal end being open; and an outer member, said outer member substantially surrounding the inner member and having an air passage therebetween said outer member having a proximal end, said proximal end being open and wherein said inner member has at least one opening therethrough into said air passage, and said outer member has at least one opening therethrough into said air passage, to enable the gas flow between the tube and the atmosphere through the openings and the air passge when said proximal end of the inner and outer members ae obstructed.

* * * * *